United States Patent [19]

Crichlow

[11] Patent Number: 5,196,432

[45] Date of Patent: Mar. 23, 1993

[54] MECHANISM MEDIATING RUMINAL STASIS IN RUMINAL LACTIC ACIDOSIS

[76] Inventor: Eugene C. Crichlow, 25 Moxon Crescent, Saskatoon, Saskatchewan, Canada, S7H 3B8

[21] Appl. No.: 480,010

[22] Filed: Feb. 14, 1990

[30] Foreign Application Priority Data

Feb. 21, 1989 [CA] Canada .................. 592375

[51] Int. Cl.$^5$ .................. A61K 31/505; A61K 31/44; A61K 31/415
[52] U.S. Cl. .................. 514/274; 514/285; 514/396; 514/401
[58] Field of Search .............. 514/401, 396, 285, 274; 548/335

[56] References Cited

U.S. PATENT DOCUMENTS

| | | | |
|---|---|---|---|
| 2,161,938 | 6/1939 | Sonn | 548/355 |
| 4,112,069 | 9/1978 | Huber | 424/93 |
| 4,172,127 | 10/1979 | Huber | 424/93 |
| 4,359,474 | 11/1982 | Anderson et al. | 514/406 |
| 4,454,139 | 6/1984 | Ward et al. | 514/294 |
| 4,473,572 | 9/1984 | Ward | 514/306 |
| 4,481,200 | 11/1984 | Ward et al. | 514/233.2 |
| 4,526,967 | 7/1985 | Ward | 546/95 |
| 4,550,114 | 10/1985 | White | 514/294 |
| 4,604,398 | 8/1986 | Ward | 514/294 |
| 4,616,017 | 10/1986 | Baldwin et al. | 514/252 |
| 4,640,916 | 2/1987 | Mequro et al. | 514/224.2 |
| 4,640,924 | 2/1987 | White et al. | 514/291 |
| 4,652,642 | 3/1987 | De Marinis | 540/594 |
| 4,683,229 | 7/1987 | Demarinis et al. | 514/213 |
| 4,686,226 | 8/1987 | Huff et al. | 514/285 |
| 4,689,339 | 8/1987 | Karjalainen et al. | 514/396 |
| 4,690,928 | 9/1987 | Huff et al. | 514/285 |
| 4,704,382 | 11/1987 | Chorvat et al. | 514/85 |
| 4,710,504 | 12/1987 | Baldwin et al. | 514/267 |
| 4,717,731 | 1/1988 | White et al. | 514/291 |
| 4,738,979 | 4/1988 | Calderan et al. | 514/396 |
| 4,788,202 | 11/1988 | Ward | 514/285 |

FOREIGN PATENT DOCUMENTS

| | | |
|---|---|---|
| B-23277/84 | 7/1984 | Australia . |
| 1059815 | 8/1979 | Canada . |
| 1135265 | 11/1982 | Canada . |
| 1156147 | 11/1983 | Canada . |
| 0076089A2 | 4/1983 | European Pat. Off. . |
| 0154142A1 | 9/1985 | European Pat. Off. . |
| 2477647 | 5/1986 | European Pat. Off. . |
| 0204254A3 | 12/1986 | European Pat. Off. . |
| 0233728A1 | 8/1987 | European Pat. Off. . |
| 0238753A1 | 9/1987 | European Pat. Off. . |

OTHER PUBLICATIONS

Chemical Abstracts (108:15047w) 1988.
Chemical Abstracts (110: 16970t) 1989.
Chemical Abstracts (111: 90310p) 1989.
Chemical Abstracts (110: 18409q) 1988.
Chemical Abstracts (106: 96101q) 1986.
Chemical Abstracts (105: 35481w) 1986.
Chemical Abstracts (102: 160313g) 1984.
Nicholson et al., "Inhibition of Rumination in Sheep by α-Adrenoreceptor Antagonists", J. Vet. Pharmacol. Therap. 11:276–282 (1988).
Ruckebusch, "Pharmacology of Reticulo-Ruminal Motor Function", J. Vet. Pharmacol. Therap. 6:245-272 (1983).

Primary Examiner—Frederick E. Waddell
Assistant Examiner—K. Weddington
Attorney, Agent, or Firm—Finnegan, Henderson, Farabow, Garrett & Dunner

[57] ABSTRACT

Ruminal lactic acidosis develops in ruminant animals following the ingestion of large amounts of unaccustomed feeds that are rich in readily fermentable carbohydrates. Characteristics symptoms of this disease include systemic acidosis, ruminal acidosis, forestomach stasis or forestomach hypomotility, inappetence, depression and hemoconcentration. Alpha-2 adrenoceptor antagonists have been found to be capable of re-establishing forestomach motility that has been lost or severely diminished in ruminants suffering from ruminal lactic acidosis. These antagonist compounds have also been found to be effective in the treatment of ruminants experiencing ruminal lactic acidosis.

10 Claims, 4 Drawing Sheets

OTHER PUBLICATIONS

Ruckebusch et al., "Depression of Reticulo-Ruminal Motor Functions Through the Stimulation of $a_2$-Adrenoceptors", J. Vet. Pharmacol. Therap. 10:1–10 (1987).

Bueno et al., "Influence of Dopamine on Rumino-Reticular Motility and Rumination in Sheep", J. Vet. Pharmacol. Therap. 6: 93 (1983).

Toutain et al., "Assessment of Alpha-2 Adrenergic Antagonists on the Central Nervous System Using Reticular Contraction in Sheep as a Model", J. Pharmacol. Exp. Therap. 223: 215–218 (1982).

Ruckebusch et al., "Specific Antagonism of Xylazine Effects on Reticulo-Rumen Motor Function in Cattle", Veterinary Med. Review, 1: 3–12 (1984).

T. J. Hopkins, "The Clinical Pharmacology of Xylazine in Cattle", Australian Veterinary Journal, 48: 109–112 (1972).

MECHANISM MEDIATING RUMINAL STASIS IN RUMINAL LACTIC ACIDOSIS

BACKGROUND AND PRIOR ART

This invention relates to the treatment of ruminal lactic acidosis in ruminant animals. Specifically, this invention relates to the use of alpha-2 adrenoceptor antagonists in the treatment of ruminant animals suffering from ruminal lactic acidosis.

One embodiment of this invention is directed towards the restoration by alpha-2 adrenoceptor antagonists of forestomach contractions in ruminants with ruminal stasis (forestomach atony) or forestomach hypomotility caused by ruminal lactic acidosis. Another embodiment of this invention is directed towards the overall use of alpha-2 adrenoceptor antagonists in the treatment of ruminant animals suffering from ruminal lactic acidosis.

Ruminal lactic acidosis (also referred to as grain overload, rumen overload, carbohydrate engorgement, feedlot founder or D-lactic acidosis) develops in ruminant animals following the ingestion of large amounts of unaccustomed feeds that are rich in readily fermentable carbohydrates. This disease occurs most commonly in ruminant livestock, for example, sheep, feedlot cattle and dairy cows, that are maintained on high energy rations. Characteristic symptoms of this disease include systemic acidosis, (decreased blood pH), ruminal acidosis, (decreased pH of rumen contents), ruminal stasis or forestomach hypomotility, inappetence, depression, and hemoconcentration. These symptoms, reportedly, result from the accumulation of toxic levels of non-metabolized D-lactic acid that are produced by abnormal fermentation in the forestomach. At present, the recommended treatments for this disease involve ruminal lavage and/or rumenotomy and intravenous infusions of bicarbonate to correct the systemic acidosis.

Many members of the family of compounds known as alpha-2 adrenoceptor antagonists have been reported in the prior art to function as antidepressants and antihypertensives (see U.S. Pat. Nos.: 4,710,504; 4,686,226; 4,616,017; 4,652,642; 4,640,924; 4,717,731); and have been proposed in the treatment of asthma, diabetes and migraine (see Patents: EP-247764A, J62289566-A); as well as in the treatment of diarrhoea (see Canadian Patent 1,156,147 dated Nov. 1, 1983). However, none of these compounds have, previously, been reported to restore contractions of the forestomach of ruminant animals that are experiencing ruminal stasis or forestomach hypomotility caused by ruminal lactic acidosis, nor have these compounds been proposed for the treatment of ruminants suffering from ruminal lactic acidosis.

Another approach to this problem has been disclosed in U.S. Pat. Nos. 4,112,069 and 4,172,127. In the method of these prior arts, the microorganism *Peptococcus asaccharolyticus* was introduced into the rumen of a ruminant animal Such an animal will be substantially immediately adapted to the high energy ration or diet employed for fattening, with substantial reduction or elimination of ruminal lactic acidosis which usually occurs when a ruminant animal is abruptly supplied with and maintained on a high-energy ration or feed.

It has now been discovered that a family of compounds (alpha-2 adrenoceptor antagonists) has the ability to re-establish forestomach motility that has been lost or severely diminished in ruminants suffering from ruminal lactic acidosis These compounds have also been found to be effective in the treatment of ruminants experiencing ruminal lactic acidosis.

SUMMARY OF INVENTION

According to the present invention there is provided a veterinary composition (adapted to be administered parenterally to ruminants) for the treatment or prevention of ruminal lactic acidosis, said composition comprising at least one compound which is an alpha-2 adrenoceptor antagonist and an orally- or parenterally-acceptable carrier therefor, said composition being administerable in amounts sufficient to alleviate ruminal lactic acidosis in ruminants.

Another embodiment of the present invention is directed to a process for producing a veterinary composition in a form adapted to be administered to ruminants for the treatment or prevention of ruminal lactic acidosis, said process comprising compounding an alpha-2 adrenoceptor antagonist with an orally- or parenterally-acceptable carrier therefor, the antagonist compound being incorporated in amounts which will alleviate the symptoms of ruminal lactic acidosis in ruminants.

A further aspect of the invention is a method of preventing or treating ruminal lactic acidosis comprising administering orally or parenterally to a ruminant animal an amount of an alpha-2 adrenoceptor antagonist sufficient to prevent or alleviate ruminal lactic acidosis symptoms.

DETAILED DESCRIPTION

Figure 1:
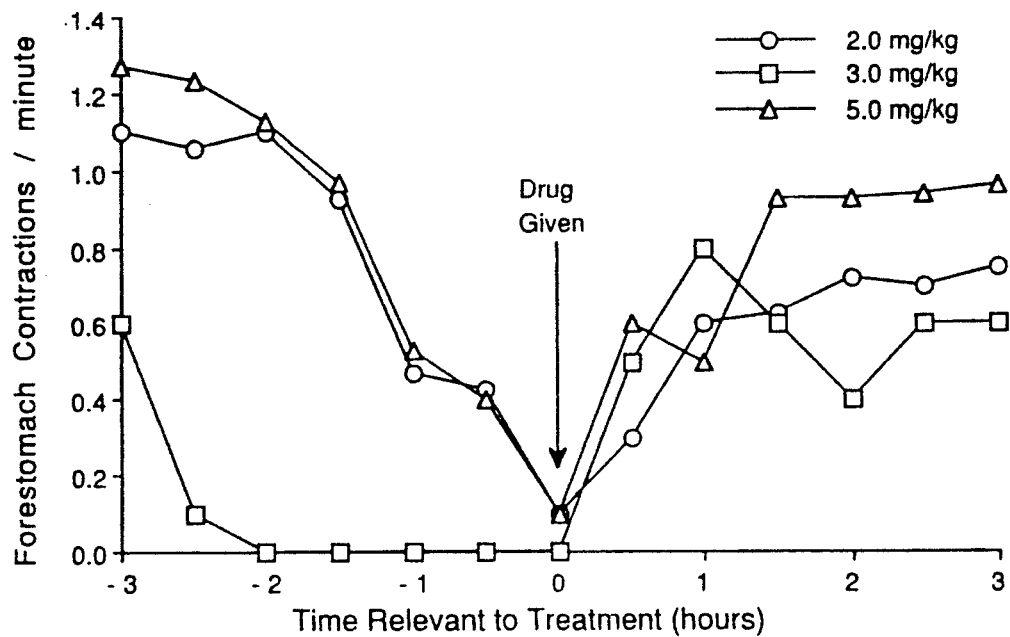
FIG. 1 shows the frequency of forestomach contractions, of sheep experiencing ruminal lactic acidosis, before and after treatment with different dosages of the alpha-2 adrenoceptor antagonist, Tolazoline (TM).

This invention relates to the treatment of ruminal lactic acidosis in ruminant animals. Specifically, this invention relates to the use of alpha-2 adrenoceptor antagonists in the treatment of ruminant animals suffering from ruminal lactic acidosis.

Examples of suitable classes of alpha-2 adrenoceptor antagonists include imidazolines, benzodioxan-imidazolines and the benzofuroquinolizines. There are a number of examples of specific alpha-2 adrenoceptor antagonists from each class known to persons skilled in the art. In the following examples the following alpha-2 adrenoceptor antagonists were tested: from the class imidazolines - Tolazoline (2-benzyl-2-imidazoline); from the class benzodioxan-imidazoline - Idazoxan [2-(1,4-benzodioxan-2-yl)-2-imidazoline hydrochloride] and MVP-1248 (Atipamezole - TM) [4-(2-ethyl-2,3-dihydro-1H-inden-2-yl) -1H-imidazole hydrochloride]; and from the class benzofuroquinolizine - L-654,248 ((2R,12bS)-N-(1,3,4,6,7,12b-hexahydro-2H-benzo[b]-furo[2,3-a]quinolizin-2-yl)-N-methyl -2-hydroxyethanesulfonamide)), and L-657,743 (2S,12bS) 1',3'-dimethylspiro-(1,3,4,5',6,6',7,12b-octahydro-2H-benzo[b]furo[2,3-a]quinolizine)-2,4'pyrimidine-2'-one).

A physiologically-acceptable carrier was chosen to facilitate a dispersion or a solution of the drug for formulation as an injectable. Such a carrier could be water or saline solution. In some cases, it may be necessary to add other agents to adjust tonicity and/or acidity of the composition. The administration of the veterinary composition would be parenterally, e.g. intraperitoneally, subcutaneously, intramuscularly or intravenously. The composition could be administered after the onset of ruminal lactic acidosis as in the following examples or it could be given prior to or simultaneously with the introduction of high-energy ration or feed to prevent ruminal lactic acidosis. It would also be possible to use the alpha-2 adrenoceptor antagonists as a feed-additive to prevent ruminal lactic acidosis.

Dosages should contain sufficient compound to produce an effective response when administered in a convenient manner. However, such dosages will depend on the potency of the drug being used in blocking alpha-2 adrenoceptor sites and its selectivity for alpha-2 adrenoceptor sites. Acceptable dosages for the imidazolines (Tolazoline), benzodioxanimidazolines (Idazoxan, MVP-1248) and one of the benzofuroquinolizines (L-654,284), range from about 2 to about 5 mg/kg body weight. The dosage range of the benzofuroquinolizines (L-657,743), which is highly selective for alpha-2 adrenoceptor sites, was about 50 to 100 μg/kg.

Dosage unit forms are very convenient, e.g. 25-50 ml of a 5-10% solution in saline of Tolazoline, Idazoxan, MVP-1248 or L-654,284 will provide a single dose for an average steer of 500 kg. Such a dose given every 6 hrs for two days will alleviate the symptoms in ruminants having this problem.

Dosage unit forms of the benzofuroquinolizine L-657,743 may be for example from 0.5-1 ml of a 5%-10% solution in physiological saline, which would provide a single dose for an average steer of 500 kg.

EXAMPLE 1

Experimental Trials a) Surgical Preparation of Animals and Induction of Ruminal Lactic Acidosis—Fifteen adult sheep (36-50 kg) and seven calves (94-130 kg) were anaesthetized and fitted with permanent rumen cannulas. Pairs of nichrome wire recording electrodes were implanted within the walls of the reticulum and rumen to record the myoelectric discharges which preceded contractions of these forestomach regions. Strain gauge transducers were also attached to the serosal surfaces of the reticulum and rumen, close to the nichrome wire recording electrodes, to record the tension generated by contractions within these areas. Following recovery from surgery, the animals were individually housed and provided with hay, a salt block and water. One month after surgery, ruminal lactic acidosis was induced, following an 18 hr fast. Ruminal lactic acidosis was induced by placing a slurry containing ground wheat (40 g/kg body weight) or ground barley (50 g/kg) body weight) combined with a equal volume of water into the rumen, via the rumen cannula.

b) Experimental Protocol—The development of ruminal lactic acidosis was assessed on the presence of marked forestomach hypomotility or ruminal stasis, ruminal acidosis, and systemic acidosis. In addition, behavioural changes associated with ruminal lactic acidosis, i.e. anorexia and depression, were also considered. Following the development of ruminal lactic acidosis, afflicted animals were injected with one of the available alpha-2 antagonists and forestomach motility, pH of rumen contents, and pH of venous blood were monitored for changes in these variables.

c) Recording of Forestomach Motility—To assess changes in forestomach motility, recordings of myoelectrical activity and tension changes generated by reticular and ruminal contractions began 4 hr before the intra-ruminal placement of wheat or barley and continued until the experiment ended. The level of forestomach motility was assessed by the frequency of the myoelectrical discharges and the frequency and amplitude of reticular tension recordings.

d) Rumen Fluid and Venous Blood Sampling—To monitor changes in acidity of rumen contents, samples of rumen fluid were collected 15 minutes before the intra-ruminal placement of wheat or barley and at regular intervals thereafter. The pH of these samples was immediately measured and the osmolality determined in triplicate on a Model 5100C Vapour Pressure Osmometer. To determine when systemic acidosis occurred, blood samples were anaerobically obtained, at the time of rumen fluid sampling, from a polyethylene cannula located within the right jugular vein. Immediately after collection, the pH and $pCO_2$ of these venous blood samples were measured on a Corning Model 178 pH/Blood Gas Analyzer and serum $HCO_3^-$ and base excess calculated from these values.

e) Sources of alpha-2 Adrenoceptor Antagonists—Tolazoline (TM) hydrochloride was from Sigma Chemical Company (St. Louis, Mo., USA). MPV-1248 hydrochloride was from the Farmos Group Ltd. (Turku, Finland) and Idazoxan (TM) was from Reckitt and Colman Pharmaceutical Division (Hull, England). The alpha-2 antagonists L-654,284 and L-657,743 were from Merck Sharp and Dome Research Labs. (West Point, Pa., USA).

Figure 2:
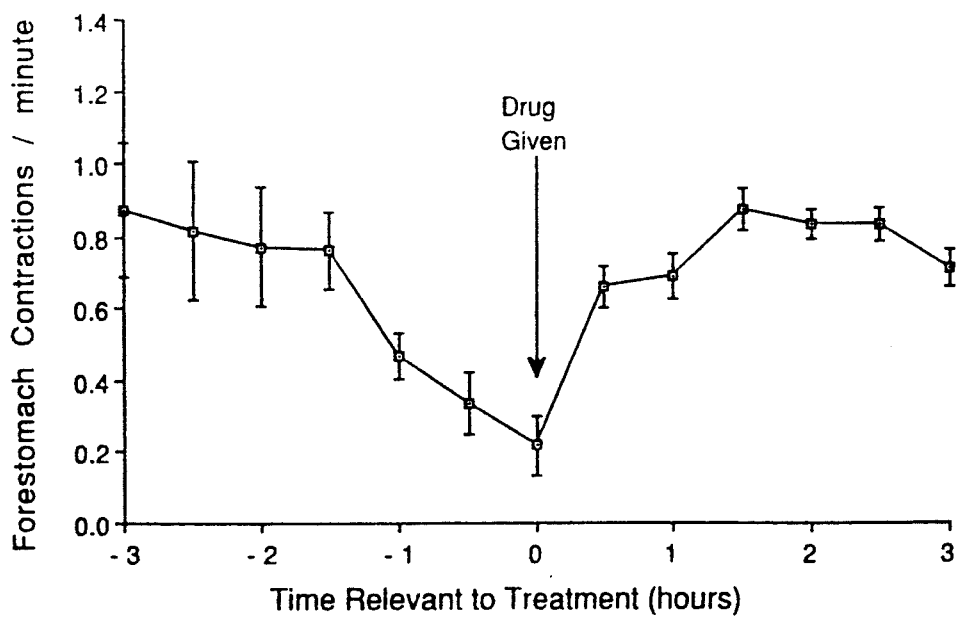
FIG. 2 illustrates the mean frequency of forestomach contractions of six sheep suffering from ruminal lactic acidosis, before and after treatment with the alpha-2 adrenoceptor antagonist, Tolazoline, at a dosage of 5.0 mg/kg. Values are expressed as the mean ± standard error measurement (SEM).
Figure 3:
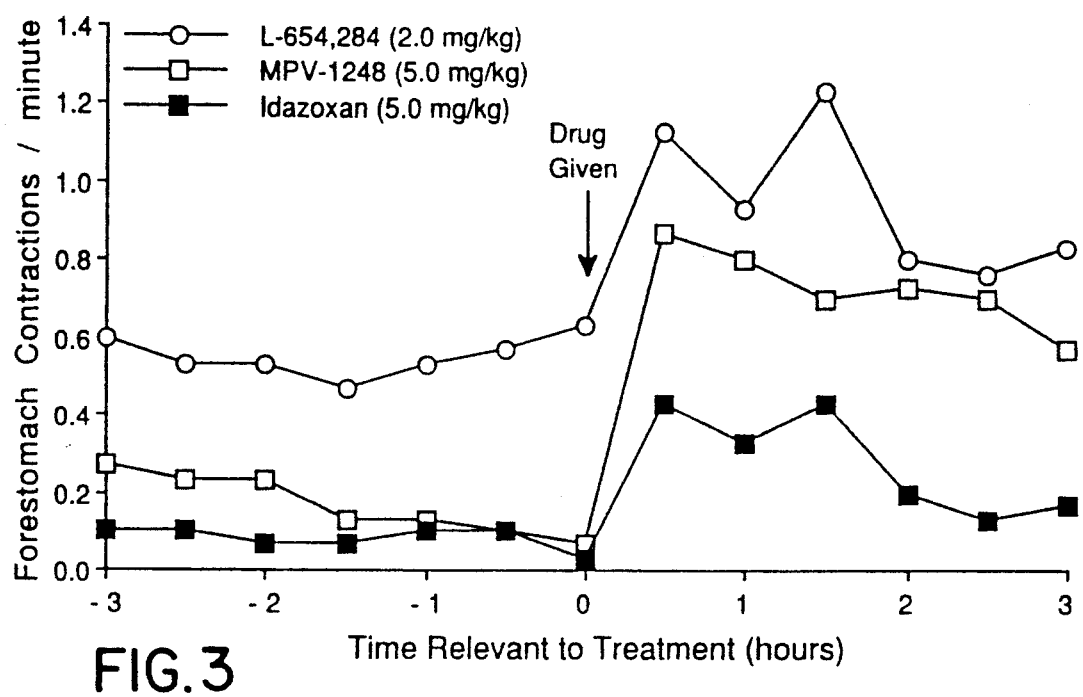
FIG. 3 depicts the effects of the administration of the alpha-2 adrenoceptor antagonists, L-654,284 (2.0 mg/kg); MPV-1248 (5.0 mg/kg) and Idazoxan (TM) (5.0 mg/kg), on the frequency of forestomach contractions of sheep suffering from ruminal lactic acidosis.
Figure 4:
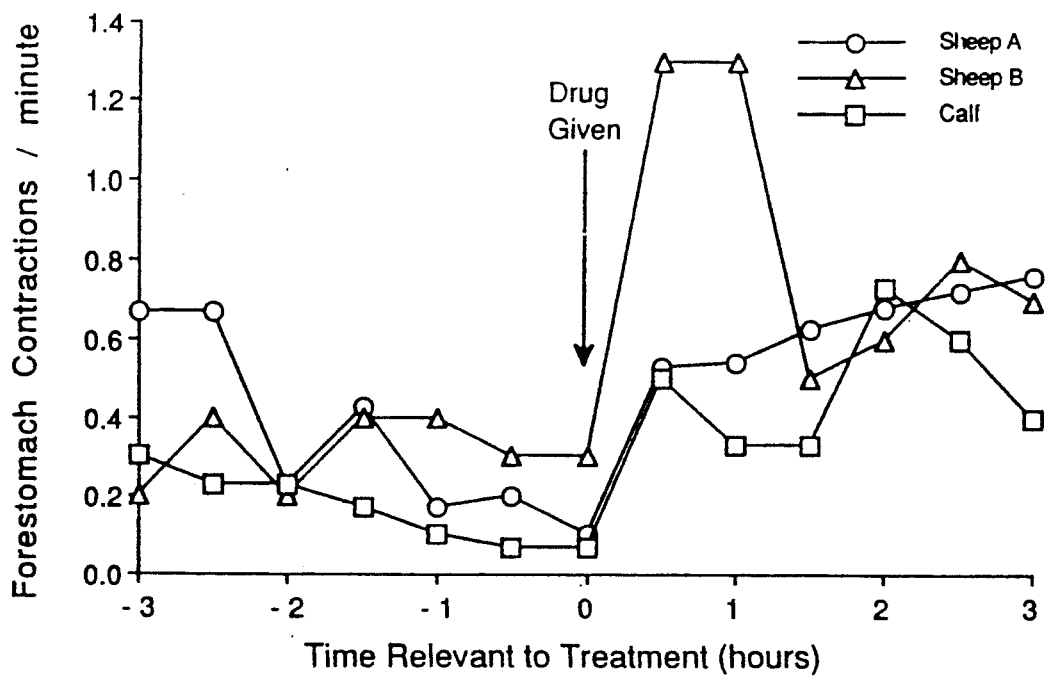
FIG. 4 shows the effects of the administration of 100 μg/kg of the alpha-2 adrenoceptor antagonist, L-657,743, on the frequency of forestomach contractions of two sheep and a calf suffering from ruminal lactic acidosis.
Figure 5:
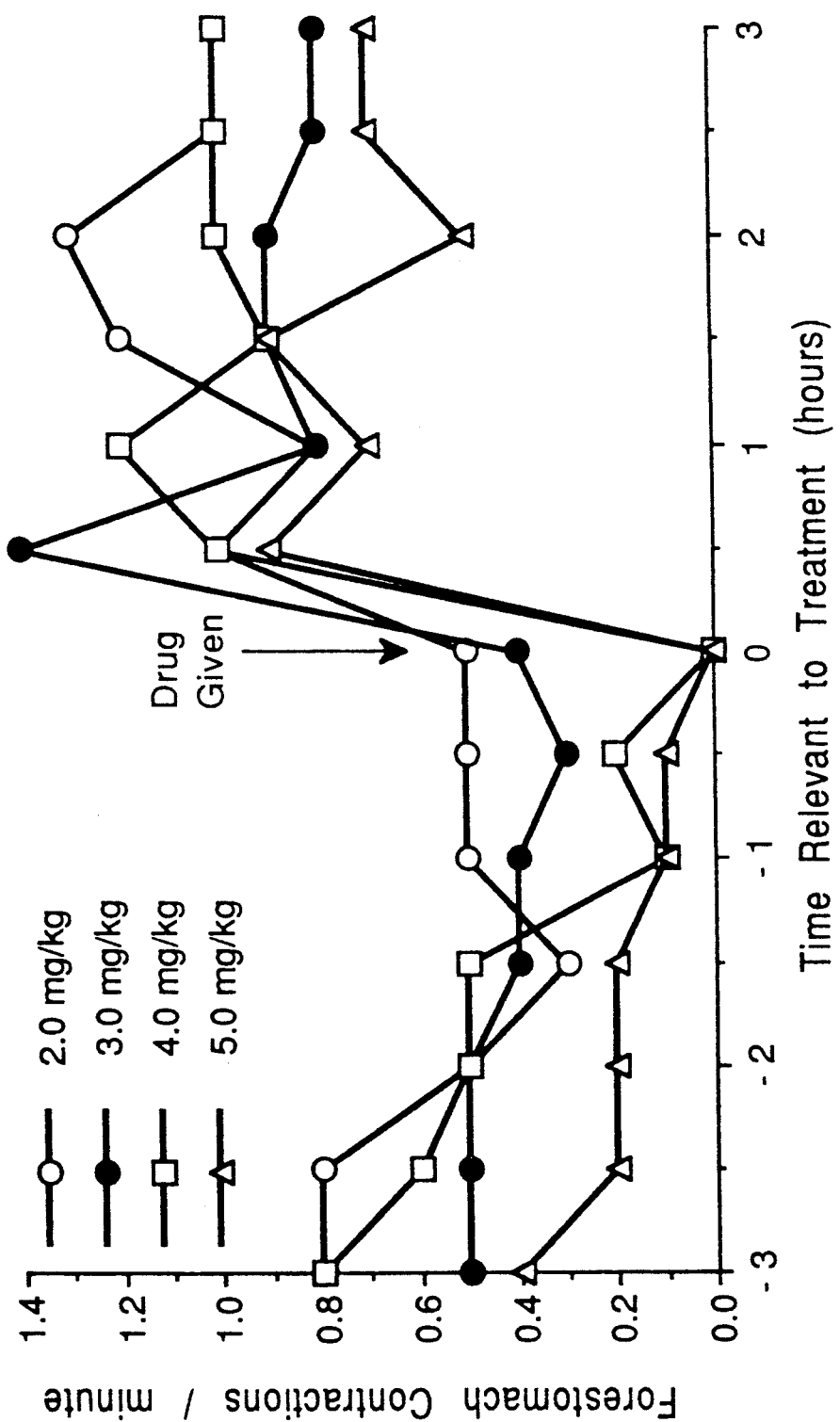
FIG. 5 illustrates the frequency of forestomach contractions, of calves experiencing ruminal lactic acidosis, before and after treatment with different dosages of the alpha-2 adrenoceptor antogonist, Tolazoline (TM).
Figure 6:
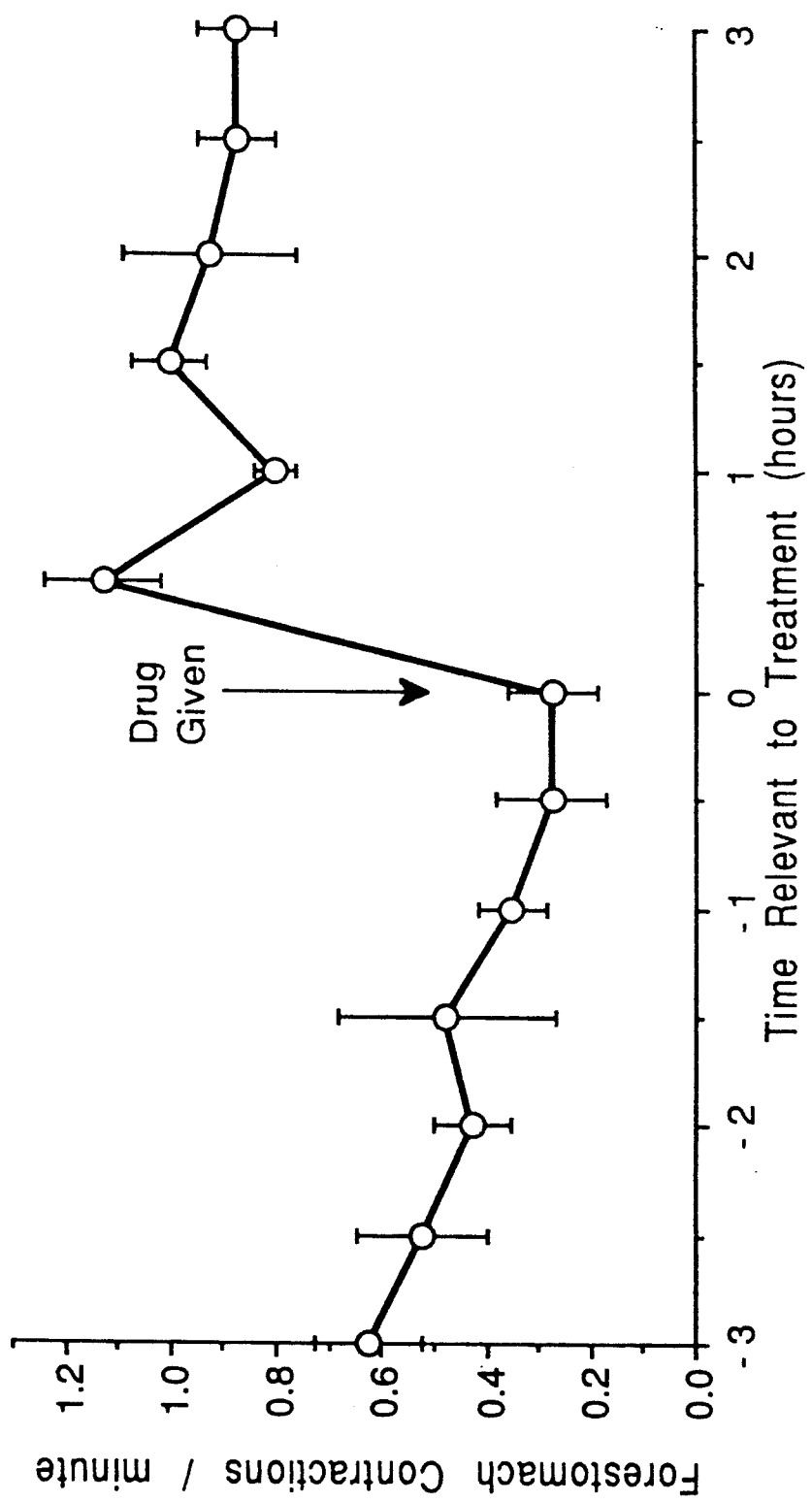
FIG. 6 depicts the mean frequency of forestomach contractions, of four calves suffering from ruminal lactic acidosis, before and after treatment with the alpha-2 adrenoceptor antagonist, Tolazoline (TM), at a dosage of 4.0 mg/kg. Values represent the mean ± the standard error measurement (SEM).

Results f) Effects of alpha-2 Adrenoceptor Antagonists on Ruminants Experiencing Ruminal Lactic Acidosis—Following administration of alpha-2 adrenoceptor antagonists, a significant increase in the frequency of forestomach motility was evident within half an hour of treatment. An increase in contraction amplitude was, occasionally, observed, but this was not as consistent as the increases in contraction frequency. The pH values of rumen contents and venous blood were not affected by the administration of alpha-2 adrenoceptor antagonists. All animals which received alpha-2 adrenoceptor antagonists returned to normal within 48 hr of the induction of ruminal lactic acidosis.

g) Effects of alpha-2 Adrenoceptor Antagonists on Forestomach Motility of Ruminants Experiencing Ruminal Lactic Acidosis - Examples of the increases in frequency of forestomach contractions induced by alpha-2 adrenoceptor antagonists are depicted in FIGS. 1–6. Increases in forestomach contractions obtained by doses of 2.0, 3.0 and 5.0 mg/kg of the alpha-2 antagonist, Tolazoline, in sheep experiencing ruminal lactic acidosis are depicted in FIG. 1. FIG. 2 displays the mean frequency of forestomach contractions, of six sheep suffering from ruminal lactic acidosis, before and after the administration of 5.0 mg/kg of Tolazoline. In sheep experiencing ruminal lactic acidosis, increases in forestomach motility obtained with doses of 5.0 mg/kg of the alpha-2 antagonists, Idazoxan and MPV1248 and doses of 2.0 mg/kg of the alpha-2 antagonist L654,284, can be seen in FIG. 3. FIG. 4 presents the increases in frequency of forestomach contractions, of two sheep and a calf exhibiting ruminal lactic acidosis, that were obtained with a dosage of 100 µg/kg of the highly selective alpha-2 adrenoceptor antagonist L-657,743. Increases in forestomach contractions, in calves suffering from ruminal lactic acidoses, with doses of 2.0, 3.0, 4.0 and 5.0 mg/kg of the alpha-2 antagonist, Tolazoline, are illustrated in FIG. 5. Finally, FIG. 6 demonstrates the mean frequency of forestomach contractions, of four calves suffering from ruminal lactic acidosis, before and after the administration of 4.0 mg/kg of Tolazoline.

I claim:

1. A method for the treatment or prevention of ruminal lactic acidosis, said method comprising administering to a ruminant animal an alpha-2 adrenoceptor antagonist for the purpose of preventing or treating ruminal lactic acidosis in said animal.

2. A method according to claim 1, wherein the alpha-2 adrenoceptor antagonist is selected from the classes of alpha-2 adrenoceptor antagonists consisting of: imidazolines, benzodioxanimidazolines and benzofuro- quinolines.

3. A method according to claim 2, wherein the alpha-2 adrenoceptor antagonist is selected from the group consisting of: 2-benzyl-2-imidazoline hydrochloride, 4-(2-ethyl-2,3- dihydro-1H-inden-2-yl)-1H-imidazole hydrochloride, 2-(1,4-benzodioxan-2-yl)-2-imidazoline hydro- chloride, ((2R12bS)-N-(1,3,4,6,7,12b-hexahydro-2H-benzo[b]-furo[2,3-a]quinolizin-2-yl)-N-methyl-2-hydroxy- ethanesulfonamide)) and (2S,12bS)1',3'-dimethylspiro-(1,3,4,5=,6,6',7,12b-octahydro-2H-benzo[b]furo[2,3-a]quinolizine)-2,4'-pyrimidine-2'-one.

4. A method according to claim 3, wherein administration is parenterally with a parenterally-acceptable carrier.

5. A method according to claim 4, wherein the alpha-2 adrenoceptor antagonist is selected from the group consisting of 2-benzyl-2-imidazoline hydrochloride, 4-(2-ethyl-2,3-dihydro-1H-inden-2-yl)-1H-imidazole hydrochloride, 2-(1,4-benzodioxan-2-yl)-2-imidazoline hydro- chloride and ((2R,12bS)-N-(1,3,4,6,7,12b-hexahydro-2H-benzo[b]furo[ 2,3-a]quinolizin-2-yl)-N-methyl-2-hydroxy- ethanesulfonamide)) and the effective dosage ranges from 2.0 to 5.0 mg/kg.

6. A method according to claim 4, wherein the alpha-2 adrenoceptor antagonist is (2S,12bS)1',3'-dimethylspiro(1,3,4,5',6,6',7,12b-octahydro-2H-benzo[b]furo[2,3-a]quinolizine)-2,4'-pyrimidine-2'-one and the effective dosage ranges from 50 µg/kg to 100 µg/kg.

7. A method according to claim 1, wherein administration is by injection with a carrier which is chosen to facilitate a dispersion or solution of the drug for formulation as an injectable.

8. A method according to claim 7, wherein the injection route is selected from the group consisting of intramuscular and intravenous and the frequency is about every 6 hours for about two days.

9. A method according to claim 1, wherein the administration is orally with an orally-acceptable carrier.

10. A method according to claim 4, further comprising a nutrient substance with the orally-administered mixture.

* * * * *